(12) United States Patent
Park (10) Patent No.: US 8,603,165 B2
(45) Date of Patent: Dec. 10, 2013

(54) INTRAOCULAR LENS

(76) Inventor: Kyong Jin Park, Gangnam-gu (KR)

( * ) Notice: Subject to any disclaimer, the term of this patent is extended or adjusted under 35 U.S.C. 154(b) by 726 days.

(21) Appl. No.: 12/530,242

(22) PCT Filed: Sep. 21, 2007

(86) PCT No.: PCT/KR2007/004632
§ 371 (c)(1),
(2), (4) Date: Sep. 8, 2009

(87) PCT Pub. No.: WO2008/108524
PCT Pub. Date: Sep. 12, 2008

(65) Prior Publication Data
US 2010/0063588 A1    Mar. 11, 2010

(30) Foreign Application Priority Data
Mar. 8, 2007    (KR) ................ 10-2007-0022871

(51) Int. Cl.
*A61F 2/16* (2006.01)
(52) U.S. Cl.
USPC ......... 623/6.23; 623/6.32; 623/6.39; 623/6.4; 623/6.41; 623/6.34; 623/6.42; 623/6.49
(58) Field of Classification Search
USPC ............ 623/6.32, 6.34, 6.38–6.43, 6.49, 6.13
See application file for complete search history.

(56) References Cited

U.S. PATENT DOCUMENTS

| | | |
|---|---|---|
| 4,451,938 A | 6/1984 | Kelman |
| 4,666,446 A | 5/1987 | Koziol et al. |
| 5,152,789 A | 10/1992 | Willis |
| 5,824,074 A | 10/1998 | Koch |
| 6,051,024 A | 4/2000 | Cumming |
| 6,599,317 B1 | 7/2003 | Weinschenk, III et al. |
| 6,749,634 B2 * | 6/2004 | Hanna .......................... 623/6.37 |
| 6,972,032 B2 | 12/2005 | Aharoni et al. |
| 7,048,760 B2 | 5/2006 | Cumming |
| 7,097,660 B2 | 8/2006 | Portney |
| 7,261,737 B2 * | 8/2007 | Esch et al. .................... 623/6.37 |
| 2003/0135272 A1 | 7/2003 | Brady et al. |
| 2003/0149479 A1 | 8/2003 | Snyder et al. |
| 2003/0204254 A1 | 10/2003 | Peng et al. |

(Continued)

FOREIGN PATENT DOCUMENTS

| | | | |
|---|---|---|---|
| FR | 2784575 | * 4/2000 | ............... A61F 2/16 |
| JP | 2003-509115 A | 3/2003 | |

(Continued)

OTHER PUBLICATIONS

International Search Report dated Jan. 3, 2008 issued in corresponding PCT Application No. PCT/KR2007/004632, 2 pages.

*Primary Examiner* — David H Willse
*Assistant Examiner* — Tiffany Shipmon
(74) *Attorney, Agent, or Firm* — Edwards Wildman Palmer LLP (57) ABSTRACT

Disclosed is an intraocular lens that is inserted inwardly into a capsular sac. One embodiment of the present invention provides an intraocular lens inserted inwardly into a capsular sac including an optic portion including a first optic body whose central region has a smaller thickness than a circumference of the central region and a second optic body coupled to the first optic body and whose central region has the same or higher thickness as/than the first optic body; and a haptic portion including a connection bar coupled to the optic portion and first support bar coupled to a circumference of the connection bar to be in contact with an inner surface of the capsular sac.

40 Claims, 7 Drawing Sheets

(56) References Cited

U.S. PATENT DOCUMENTS

| | | |
|---|---|---|
| 2004/0082994 A1 | 4/2004 | Woods et al. |
| 2004/0082995 A1* | 4/2004 | Woods .................. 623/6.34 |
| 2006/0001186 A1 | 1/2006 | Richardson et al. |
| 2006/0155373 A1* | 7/2006 | Israel ..................... 623/6.4 |
| 2006/0244904 A1 | 11/2006 | Hong et al. |

FOREIGN PATENT DOCUMENTS

| | | |
|---|---|---|
| JP | 2006-503661 A | 2/2006 |
| JP | 2006-511245 A | 4/2006 |
| WO | 97-43984 A1 | 11/1997 |

* cited by examiner

INTRAOCULAR LENS

TECHNICAL FIELD

The present invention relates to an intraocular lens, and more particularly to an intraocular lens provided inside a capsular sac.

BACKGROUND ART

In recent years, as one of treatment methods of ophthalmic diseases that are abnormal in eye lens such as cataract, a method has been increasingly used throughout the world, comprising steps of removing eye lens contents from a capsular sac and inserting an artificially produced intraocular lens into their space.

In the case of the insertion of the intraocular lens, the intraocular lens may give an opaque sight to patients instead of their own natural eye lens. However, regardless of its many advantages, the intraocular lens has problems that a capsular sac into which the intraocular lens is inserted is contracted after the insertion of the intraocular lens.

Accordingly, a new method has been increasingly used, comprising steps of inserting a capsular tension ring into an equatorial region of a capsular sac prior to the insertion of the intraocular lens and fixing the intraocular lens in the capsular tension ring.

A capsular tension ring, which is referred to as open or closed ring formations, is effective in partially relieving contraction of a capsular sac, partially maintaining a shape of the capsular sac from which an eye lens is removed, and easily supporting the inserted intraocular lens.

In order to use a capsular tension ring in a more effective manner, there have been recently ardent studies to develop a structure for easily inserting a capsular tension ring, a structure for preventing a posterior capsular opacity, etc.

However, a more serious problem in the conventional surgical operation of insertion of an intraocular lens is that an anterior capsule and a posterior capsule of a capsular sac are adhere to each other after the surgical operation, which leads to the loss of its inherent function to control a thickness of an eye lens by relaxing and contracting zonule of Zinn.

That is to say, the problems are that a patient does not ensure a sight through active three-dimensional movements of an intraocular lens along objects to be seen, but ensures a passive sight according to the predetermined power of an intraocular lens.

Hereinafter, the conventional surgical operation of insertion of an intraocular lens will be described in detail with reference to the accompanying drawings.

Figure 1:
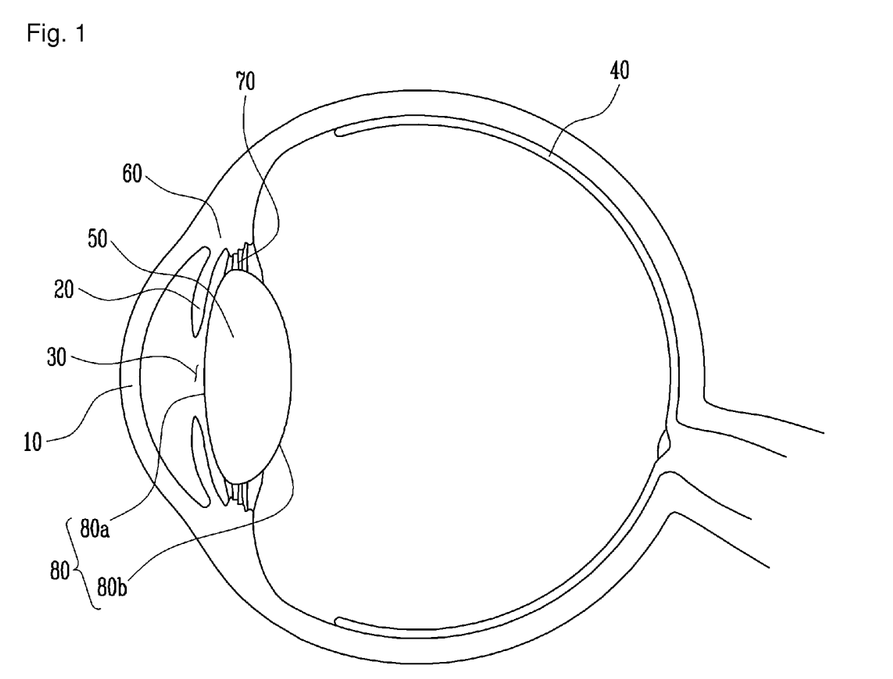
FIG. 1 is a cross-sectional view showing a human eyeball.
Figure 2:
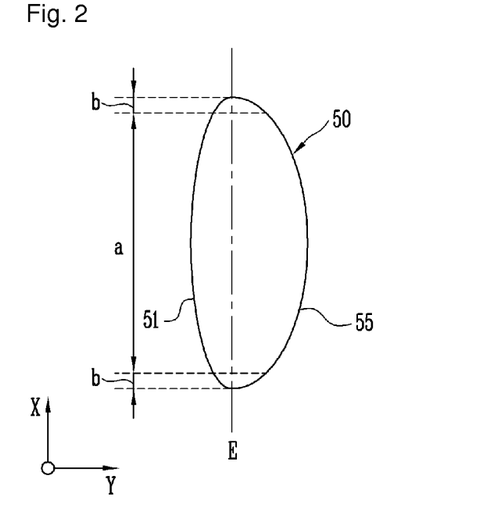
FIG. 2 is a cross-sectional view showing a structure of a natural eye lens.

FIG. 1 is a cross-sectional view showing a human eyeball, and FIG. 2 is a cross-sectional view showing a structure of a natural eye lens. Referring to FIGS. 1 and 2, a cornea 10 is a transparent avascular tissue disposed in the outermost region of the eye and protects an eyeball. Also, the cornea serves to reflect the light together with the eye lens. An iris 20 functions as the iris of a camera by adjusting the intensity of the light entering the eye. Also, a pupil 30 is a hole in the center of the iris 20, and adjusts the intensity of the light entering the retina 40 by contracting the hole under the bright light and expanding the hole under the dark light.

An eye lens 50 is a colorless and transparent avascular structure having a convex lens shape in both sides, and arranged in the back of the iris 20. The eye lens 50 is an organ that takes part in reflecting the light entering the eye together with the cornea 10, and its shape is changed according to the contraction and relaxation of a ciliaris muscle 60 and a zonule of Zinn 70 coupled to the ciliaris muscle 60.

Presbyopia is a state that the hardness of the eye lens 50 increases with the age, and therefore the shape of the eye lens 50 is not changed even if the ciliaris muscle 60 contracts, and the cataract is a disease that the eye lens 50 becomes opaque with the age.

The eye lens 50 is filled inside a capsular sac 80, and the capsular sac 80 is composed of an anterior capsule 80a and a posterior capsule 80b, each of which is in contact with an anterior surface 51 and a posterior surface 55 of the eye lens 50. At this time, the anterior surface 51 and the posterior surface 55 of the eye lens 50 are coupled to each other in an equator (E). Each of the anterior surface 51 and the posterior surface 55 is divided into a central region (a) and an equatorial region (b) according to the distance from the equator (E). The central region (a) of the anterior surface 51 has a smaller curvature than the central region (a) of the posterior surface 55, and the equatorial region (b) of the anterior surface 51 has a larger curvature than the equatorial region (b) of the posterior surface 55.

The zonule of Zinn 70 is coupled along an edge of the capsular sac 80. The zonule of Zinn 70 is a kind of a fibrous tissue that couples the capsular sac 80 to the ciliaris muscle 60, and composed of a first zonule portion coupled to the center of the equatorial region in which the anterior capsule 80a and the posterior capsule 80b of the capsular sac 80 meets; and a second zonule portion coupled to a circumference of the equatorial region.

Figure 3:
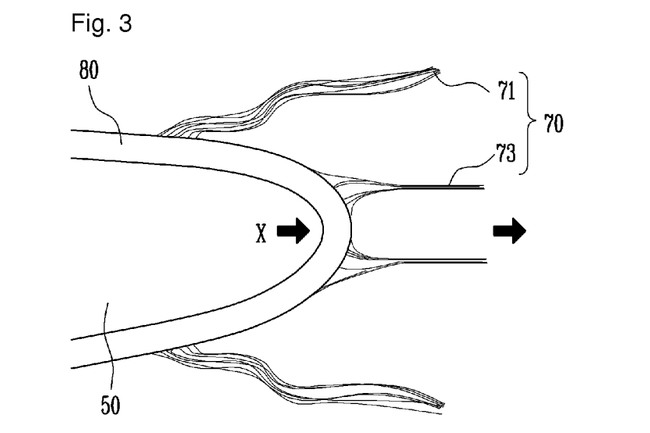
FIG. 3 and FIG. 4 are illustrative views showing interactions a zonule of Zinn and an eye lens when focused on a long distance and a short distance object, respectively.
Figure 4:
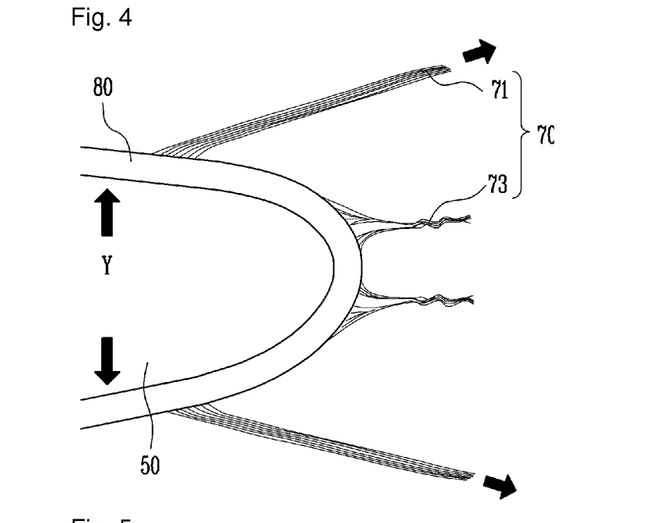

FIG. 3 and FIG. 4 are illustrative views showing an interaction of a zonule of Zinn, an eye lens and a capsular sac when focused on a long distance and a short distance object, respectively. In this application, a Y direction represents a visual axis direction of an eye lens, and an X direction represents an equatorial direction of an eye lens. The visual axis direction of the eye lens means a direction that the light enters an eye lens 50 through a pupil, and the equatorial direction means a direction that, as a vertical direction of the visual axis direction, connects a point that an anterior capsule and a posterior capsule of an eye lens meets.

In the zonule of Zinn 70, a first zonule portion 73 coupled to the center of the equatorial region of the capsular sac 80 is pulled taut and a second zonule portion 71 coupled to the circumference of the equatorial region of the capsular sac 80 is relaxed when focused on a long distance object. As a result, the capsular sac 80 is extended in an X direction of the eye lens 50, and therefore the eye lens 50 arranged inside the capsular sac 80 is extended in the same direction (X).

In the zonule of Zinn 70, the first zonule portion 73 coupled to the center of the equatorial region of the capsular sac 80 is relaxed and the second zonule portion 71 coupled to the circumference of the equatorial region of the capsular sac 80 is pulled taut when focused on a short distance object. As a result, the capsular sac 80 is projected in a Y direction of the eye lens 50, and therefore the eye lens 50 arranged inside the capsular sac 80 is extended in the same direction. As described above, the capsular sac 80 having a natural eye lens disposed therein is coupled to the zonule of Zinn 70, and therefore takes part in actively deforming shapes of the natural eye lens, but the use of the conventional intraocular lens and capsular tension ring forces the capsular sac to contract, which leads to the substantial loss of its functions.

In particular, a ciliaris muscle, which is coupled to a zonule of Zinn to take part in the shape deformation of an eye lens, is a visceral muscle that maintains the endless function to the death. Therefore, the conventional method of artificially removing an ability of healthy ciliaris muscle must be improved in that an ability of ciliaris muscle is not damaged although the eye lens is damaged.

Meanwhile, the conventional intraocular lens and capsular tension ring are disclosed in various literatures including U.S. Patent Publication Nos. 2006/0244904, 2006/0001186 and 2003/0149479.

DISCLOSURE OF INVENTION

Technical Problem

Accordingly, the present invention is designed to solve such drawbacks of the prior art, and therefore an object of the present invention is to provide an intraocular lens that is configured so that an intraocular lens moves similarly to a natural eye lens.

Technical Solution

One embodiment of the present invention is achieved by providing an intraocular lens inserted inwardly into a capsular sac including an optic portion including a first optic body whose central region has a smaller thickness than a circumference of the central region and a second optic body coupled to the first optic body and whose central region has the same or higher thickness as/than the first optic body; and a haptic portion including a connection bar coupled to the optic portion and first support bar coupled to a circumference of the connection bar to be in contact with an inner surface of the capsular sac.

At this time, the first optic body may be made of materials that are more flexible than the second optic body.

Also, the first optic body may include an inner surface and an outer surface and the inner surface and the outer surface may be a spherical surface or an aspheric surface, and the inner surface is preferably a spherical surface having a higher curvature than the outer surface, or a more aspheric surface than the outer surface.

Also, the first support bar preferably has a surface that is in contact with an inner surface of the capsular sac and has a round shape.

Also, the connection bar is preferably a shaft bar-shaped structural body coupled to at least two sections in a circumference of the optic portion.

Also, the first support bar is preferably a structural body for coupling at least two ends of the shaft bars arranged opposite to the optic portion of the connection bar.

Also, the first support bar is preferably a ring-shaped structural body for coupling all ends of the shaft bars arranged opposite to the optic portion of the connection bar.

Also, ends of the optic portion of the shaft bar preferably include a second support bar for coupling ends of the optic portion.

Also, both ends of the shaft bar preferably have a larger cross-sectional area than a central region of the shaft bar.

Also, an inner surface of the second support bar preferably has a concave shape toward the central region of the optic portion.

Also, the second support bar may be coupled to a circumference of the optic portion.

Also, the second support bar is preferably inserted inwardly into the optic portion.

Also, the connection bar is preferably a disk-shaped structural body coupled to the entire section of the circumference of the optic portion.

Also, the connection bar is preferably a disk-shaped structural body coupled to at least two sections of the circumference of the optic portion and divided into at least two sections.

Also, the first support bar may be formed around an end of the disk-shaped connection bar.

Also, the optic portion and the first support bar may be made of flexible materials that is more flexible than a material of the connection bar.

Also, the optic portion and the first support bar may be made of the same flexible materials as the connection bar, and formed in a thinner thickness than the connection bar.

Also, the first support bar may be a structural body that is extended along an end of the connection bar, and may include a first face coming in contact with the inner surface of the capsular sac in at least one point; and a second face arranged opposite to the first face, and the first face may be provided at a length as much as 3/4 to 3 times of a length (d5, d10) of a region where a zonule of Zinn is coupled to an outer surface of the capsular sac in a section where the first support bar is cut along a virtual plane in a visual axis direction (Y direction) of an eye lens.

Also, the first face may be made of flexible materials that more flexible than the second face.

Also, the first face may be made of the same flexible materials as the second face, and formed in a thinner thickness than the second face.

Also, the first face may be made of the same flexible materials as the second face, and formed in the same thickness as the second face.

Also, a surface of the first face may be rougher than the other surface.

Also, the surface of the first face may further include an adhesive for facilitating mounting of the capsular sac.

Also, the adhesive is preferably a tissue glue or a glue.

Also, a flowing space is preferably provided inside the intraocular lens.

Also, the flowing space is preferably provided at least between the first optic body and the second optic body.

Also, the flowing space preferably includes a first space portion provided between the first optic body and the second optic body; a second space portion provided inside the connection bar; and a third space portion provided inside the first support bar.

Also, the first space portion, the second space portion and the third space portion may be coupled to each other.

Also, the flowing space is preferably filled with one selected from the group consisting of liquid, gas, and fluent solid.

Also, the liquid is preferably one selected from the group consisting of water, silicone, sodium hyaluronate, chondroitin sulfate, hydroxypropyl methylcellulose and polyacrylamide.

Also, the gas is preferably one selected from the group consisting of air, nitrogen, helium, neon and argon.

Also, at least one face out of the first face and the second face is preferably protruded in a direction from the second face toward the first face.

Also, the first face preferably has an anterior portion and a posterior portion divided by an equator, which correspond respectively to an anterior capsule and a posterior capsule of the capsular sac, and the anterior portion preferably has a larger curvature than the posterior portion.

Also, the first face of the first support bar preferably has an extended length (d1) from the equator to an end point of the anterior portion and an extended length (d2) from the equator to an end point of the posterior portion, and the extended lengths (d1, d2) preferably range from 1 to 4.2 mm in the section where the intraocular lens is cut along a virtual plane in a visual axis direction (Y direction) of the eye lens.

Also, the extended length (d1) from the equator to the end point of the anterior portion is preferably smaller than the extended length (d2) from the equator to the end point of the posterior portion.

Also, a sectional shape of the first face of the first support bar preferably accords with an inner surface of the capsular sac when the sectional shape of the first face is in contact with the inner surface of the capsular sac in the section where the intraocular lens is cut along a virtual plane in a visual axis direction (Y direction) of the eye lens.

Also, the first space portion preferably has at least one convex surface.

Also, the first space portion preferably has at least one aspheric surface.

Also, the second optic body preferably has a thinner thickness in its central region than its circumference.

Also, the second optic body preferably includes an inner surface and an outer surface, and the inner surface and the outer surface may be spherical surface or an aspheric surface, and the inner surface is preferably a spherical surface or an aspheric surface that has a larger curvature than the outer surface.

Also, the first optic body and the second optic body preferably have the same thickness, and preferably include sections that have an increasing thickness as their central regions approach their circumference, respectively.

Also, a material of the intraocular lens is preferably composed of one selected from the group consisting of silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Also, the first optic body preferably includes a section that grows thicker as its equatorial region approaches its circumference.

ADVANTAGEOUS EFFECTS

The intraocular lens according to the present invention has an effect to transfer a force to the intraocular lens, which is inserted inwardly into the ciliaris muscle, to allow the intraocular lens to operate like the natural eye lens, the force being generated from the ciliaris muscle and transferred through the zonule of Zinn and the capsular sac.

Accordingly, the intraocular lens according to the present invention may be used for the intraocular lens operation used to treat cataract, presbyopia, high myopia, etc.

BRIEF DESCRIPTION OF THE DRAWINGS

These and/or other aspects and advantages of the invention will become apparent and more readily appreciated from the following description of the preferred embodiments, taken in conjunction with the accompanying drawings of which.

MODE FOR THE INVENTION

Hereinafter, preferable embodiments according to the present invention will be described with reference to the accompanying drawings. Here, when one element is connected to another element, one element may be not only directly connected to another element but also indirectly connected to another element via another element. Further, irrelative elements are omitted for clarity. Also, like reference numerals refer to like elements throughout.

Figure 5:
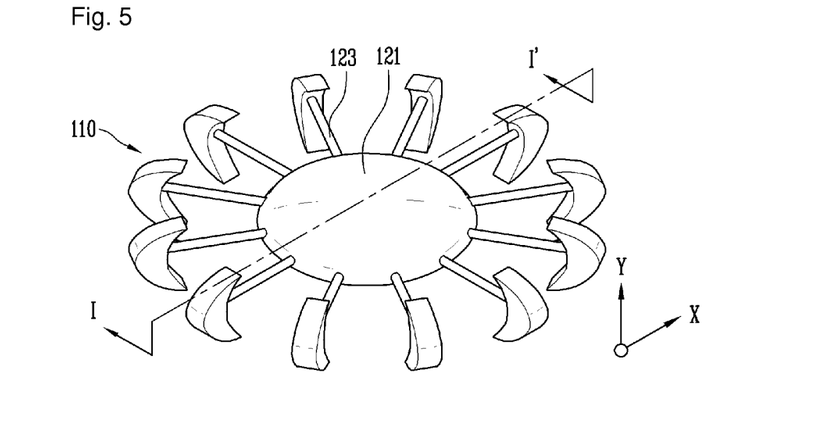
FIG. 5 is a perspective view showing an intraocular lens supporter according to the first embodiment of the present invention.
Figure 6:
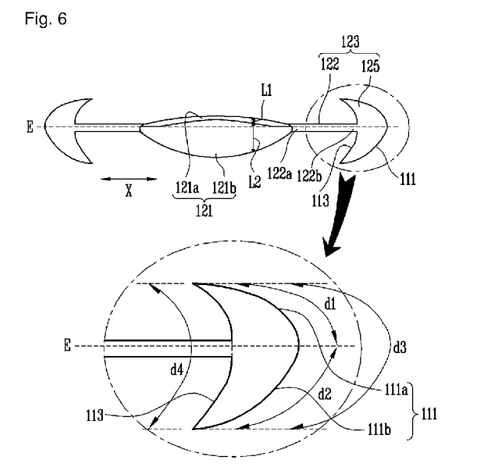
FIG. 6 is a cross-sectional view taken from a line I-I' as shown in FIG. 5.

FIG. 5 is a perspective view showing one embodiment intraocular lens (IOL) according to one embodiment of the present invention, and FIG. 6 is a cross-sectional view taken from a line I-I' as shown in FIG. 5.

Referring to FIGS. 5 and 6, the intraocular lens 110 is an artificial eye lens that is inserted inwardly into a capsular sac, and the intraocular lens 110 according to this embodiment is divided into an optic portion 121 and a haptic portion 123.

The optic portion 121 is a portion that is arranged in the rear of a pupil in the eye and functions as a lens of a natural eye lens in a hard lens, and it has a convex lens shape (but, a concave lens shape in some extremely myopic patients).

The optic portion 121 includes a first optic body 121a that has an increasing thickness as its central region approaches its circumferential region, and a second optic body 121b coupled to the first optic body 121a, wherein a thickness of a central region of the second optic body 121b is identical to or thicker than the first optic body 121a.

At this time, an inner surface of the first optic body 121a is a spherical surface having a larger curvature than an outer surface, or a more aspheric surface.

Also, the first optic body 121a and the second optic body 121b may have different convexity. That is to say, the first optic body 121a and the second optic body 121b may be different from each other like an anterior surface and a posterior surface of a human eye lens, but a curvature of the anterior surface is preferably smaller than the posterior surface.

Meanwhile, shapes of the optic portion 121 are not limited thereto, but the optic portion 121 is preferably provided in a conventional convex lens shape. In this case, a diameter of the optic portion 121 may be provided in a diameter as much as 0.2 to 0.8 times of the total diameter of the intraocular lens 110.

To constitute an optic portion 121 composed of two pieces of a first optic body 121a and a second optic body 121b is for the purpose of facilitating a shape deformation of the optic portion 121.

A thickness (L1) of the first optic body 121a is smaller than a thickness (L2) of the second optic body 121b in the section cut along a virtual plane in a visual axis direction (Y direction) of the eye lens. This is for the purpose that the shape deformation of the first optic body 121a is more induced than the second optic body 121b as if the shape deformation of the anterior surface is actually higher in the eye lens if a mechanical or fluent force is transferred to the optic portion 121, as described later.

Also, unlike the first optic body 121a, the thickness (L2) of the second optic body 121b is desirably thicker in its central region in a mechanical manner as described later, but the thickness (L2) is preferably increased as the central region approaches the circumferential region if the front and rear surfaces of the central region ensure a flowing space with an aspheric surface while enhancing its functions using as an oil pressure manner as described later. This is also for the purpose that the optic portion has a structure of a natural eye lens, and the central region of the optic portion makes it easier to make shape deformation than the circumferential region, thereby to function more similarly to the natural eye lens.

The haptic portion 123 is coupled to the optic portion 121 from an edge region of the optic portion 121, and the haptic portion 123 has a plurality of shaft bars 122. The shaft bars 122 of the haptic portion 123 are provided in at least two numbers to transfer a force to the intraocular lens 110 in balance. In this embodiment, an end 122b arranged opposite to the optic portion of the shaft bar 122 further includes a support bar 125 that is in contact with an inner surface of a capsular sac (not shown) (or, if an intraocular lens supporter is provided, an inner surface of the intraocular lens supporter (hereinafter, referred to as an inner surface of a capsular sac) means including an inner surface of the intraocular lens supporter). The support bar includes a first face 111 and a second face 113, each of which is extended from the end 122b of the shaft bar 122.

The first face 111 is in contact with an equatorial region of the capsular sac in at least one point, and the second face 113 is formed to face the first face 111 and coupled to the end 122b arranged opposite to the optic portion of the shaft bar 122. At this time, at least the first face 111 is protruded in a direction from the second face 113 toward the first face 111, namely a direction from the inside toward the outside of the capsular sac.

Also, the first face 111 has an anterior portion 111a and a posterior portion 111b that are divided by the equator (E) to correspond respectively to the anterior capsule and the posterior capsule of the capsular sac.

At this time, in a section where the optic portion of the intraocular lens 110 is cut along a virtual plane in a visual axis direction (Y direction) of the eye lens visual axis direction, the anterior portion 111a of the first face 111 has a larger curvature than the posterior portion 111b. This is why the section where the first face 111 is cut along a virtual plane in a visual axis direction (Y direction) of the eye lens is formed in the same shape as a sectional shape of an equatorial region of a natural eye lens. As described above, the anterior surface in the central region of the eye lens has a smaller curvature than the posterior surface, but has a reverse shape as it approaches an equatorial region. More particularly, the first face 111 is formed in the same sectional shape as the inherent eye lens of a patient that undergoes a surgical operation. A photograph of a sectional shape of the patient eye lens before the surgical operation may be taken using ultrasonic imaging, CT, and MRI. The first face 111 has a sectional shape between mydriasis and miosis, but may have a shape that accord with the sectional shape of the eye lens having a pupil size of 3 to 4 mm.

Accordingly, the first face 111 accords with a shape of the inner surface in the equatorial region of the capsular sac.

In the section cut along a virtual plane in a visual axis direction (Y direction) of the eye lens, the first face 111 is preferably provided in a length as much as ¾ to 3 times of a length (d5, see FIG. 7) of a region where a zonule of Zinn is coupled to an outer surface of the capsular sac. A force transferred to the intraocular lens with the movement of the zonule of Zinn is not effectively transferred if the first face 111 is formed in a smaller length range than ¾ times, and an optic portion of the intraocular lens may be covered if the first face 111 is formed in a smaller length range than 3 times.

More preferably, an extended length (d1) from the equator (E) to an end point of the anterior portion 111a, and an extended length (d2) from the equator (E) to an end point of the posterior portion 111b may generally range from 1 to 4.2 mm in the section where the eye lens of the intraocular lens 110 is cut along a virtual plane in a visual axis direction (Y direction) of the eye lens. It is difficult to insert the intraocular lens supporter in the surgical operation and the optic portion is too small if the extended length exceeds 4.2 mm, whereas the support bar 125 is provided in an inner position than a point where the second zonule portion 171 of the zonule of Zinn is coupled to the capsular sac if the extended length is less than 1 mm, and therefore a force is not suitably transferred to the intraocular lens 110 according to the movement of the zonule of Zinn induced in the ciliaris muscle, which leads to insufficient volume change in the intraocular lens 110. At this time, the total length of the section where the first face is cut along a virtual plane in a visual axis direction (Y direction) of the eye lens will range from 2 to 8.4 mm. Meanwhile, a roughness of the first face 111 may be improved or a separate adhesive may be used to facilitate mounting of the intraocular lens supporter 110 in the capsular sac. Therefore, the intraocular lens supporter 110 may be fixed in a stable position. A tissue glue or glue may be, for example, used as the adhesive.

The second face 113 is a surface to which the shaft bar 122 of the intraocular lens 110 is coupled, and the total extended length (d4) of the second face in the support bar 125 of the intraocular lens cut along a virtual plane in a visual axis direction (Y direction) of the eye lens is shorter than, or identical to the total extended length (d3=d1+d2) of the first face 111. A fact that the total extended length (d4) in a visual axis direction (Y) of the second face 113 is shorter than, or identical to the total extended length (d3=d1+d2) of the first face 111 is for the purpose of amplifying or maintaining a force transferred to the first face 111 when the force is transferred to the second face 113 in the zonule of Zinn.

That is to say, when a force FI is transferred to the zonule of Zinn in the first face 111, a force transferred to the second face 113 becomes F2 (=kF1, k≥1). At this time, k is a constant determined by a length ratio of d3 and d4. The length ratio of d3 and d4 may be varied according to the ability of the zonule of Zinn in patients, and a length of d4 is preferably longer as much as 0.4 to 1 times than a length of d3.

Meanwhile, the optic portion 121 in the intraocular lens 110 is preferably made of flexible materials that are more flexible than the materials constituting the shaft bar 122 of the haptic portion 123, or in a thinner thickness. This is for the purpose of deforming a shape of the optic portion 121 effectively by a force transferred by the movement of the zonule of Zinn that is induced in the ciliaris muscle. Here, the term flexible means that a material is so soft to deform easily.

The shaft bar 122 of the haptic portion 123 is made of a relatively more rigid material than the optic portion 121, or has suitable elasticity and restoring force for the mechanical deformation. In this case, it is possible to operate on an eye by cutting a relatively smaller eyeball.

At this time, the optic portion 121 and the haptic portion 123 are made of different materials as described above, and therefore the intraocular lens 110 may be composed of a plurality of pieces. Also, the optic portion 121 and the haptic portion 123 may be composed of the same materials, but they may have different flexibility.

Also, the flexibility of the shaft bar 122 of the haptic portion 123 may be identical to, or different from the flexibility of the support bar 125 of the haptic portion 123, and the shaft bar 122 and the support bar 125 may be composed of at least two pieces, or composed of one piece. The support bar 125 is a region that directly reflects a volume change in the intraocular lens supporter as described later according to the shape deformation of the zonule of Zinn, and therefore the shape deformation of the support bar 125 is made more effectively if the flexible materials that are more flexible than the shaft bar 122 are used.

If the intraocular lens is composed of pieces, the pieces may be attached to each other using an adhesive, a laser and a heat.

A material of the intraocular lens supporter 110, as used herein, may include silicone, silicone elastomer, silicone polymer, polydimethyl siloxane, polypropylene, polyimide, polybutester, Polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Figure 7:
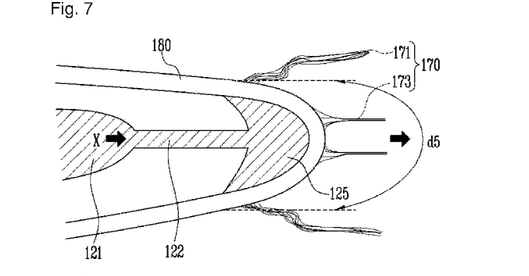
FIG. 7 and FIG. 8 are illustrative views showing interactions of a zonule of Zinn, an intraocular lens and a capsular sac when focused respectively on a long distance and a short distance object according to the first embodiment of the present invention.
Figure 8:
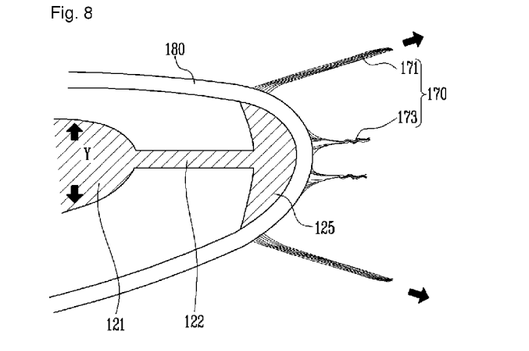

FIG. 7 and FIG. 8 are illustrative views showing interactions of a zonule of Zinn, an intraocular lens and a capsular sac when focused on a long distance and a short distance object according to the first embodiment of the present invention.

The zonule of Zinn 170 is coupled to the outer surface of the capsular sac 180, and the zonule of Zinn 170 is coupled to a region around the equator of the capsular sac 180, and therefore a region to which the zonule of Zinn 170 is coupled is referred to as a connection region for zonule of Zinn (Z) in this application.

When focused on a long distance, a first zonule portion 173 coupled to the center of the connection region for zonule of Zinn (Z) in the capsular sac 180 is pulled taut, and a second zonule portion 171 coupled to a circumference of the equatorial region of the connection region for zonule of Zinn (Z) in the capsular sac 180 is relaxed. As a result, the equatorial region of the capsular sac 180 is subject to a force generated when extended in an X direction, and the intraocular lens 120 with elasticity arranged inside the capsular sac 180 is also extended in the same direction, which leads to the convex intraocular lens 120.

When focused on a short distance object, the first zonule portion 173 coupled to the center of the connection region for zonule of Zinn (Z) in the capsular sac 180 is relaxed, and the second zonule portion 171 coupled to a circumference of the connection region for zonule of Zinn (Z) in the capsular sac 180 is pulled taut. As a result, the equatorial region of the capsular sac 180 is protruded in a Y direction, and therefore the intraocular lens 120 with elasticity arranged inside the capsular sac 180 is extended in the same direction.

As described above, the use of the intraocular lens supporter 110 according to this embodiment makes it the intraocular lens 110 possible to control its thickness like the natural eye lens. That is to say, as a thickness of the natural eye lens is controlled by the action of the capsular sac 180 coupled to the zonule of Zinn, a thickness of the intraocular lens 110 according to this embodiment may also be controlled. In particular, the intraocular lens according to this embodiment has a lower transfer ability in the movement of the zonule of Zinn, than the second embodiment, since the intraocular lens according to this embodiment is deformed mechanically only, and therefore the intraocular lens according to this embodiment will be suited for patients whose zonule of Zinn move more smoothly.

At this time, if the optic portion 121 and the support bar 125 of the haptic portion 123 are formed of more flexible materials, a shape of the intraocular lens may be easily deformed.

Figure 9:
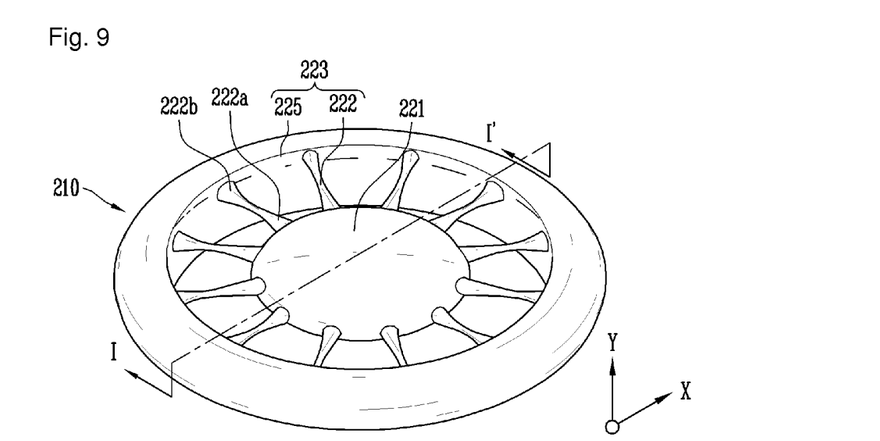
FIG. 9 is a perspective view showing an intraocular lens according to the second embodiment of the present invention.

Next, the second embodiment of the present invention will be described in detail with reference to FIG. 9. FIG. 9 is a perspective view showing one embodiment of an intraocular lens (IOL) according to one aspect of the present invention, and FIG. 10 is a cross-sectional view taken from a line I-I' as shown in FIG. 9.

In the intraocular lens according to the second embodiment, parts that are overlapped with the first embodiment will be described in brief, but part that are different from the first embodiment will be described in detail.

Figure 10:
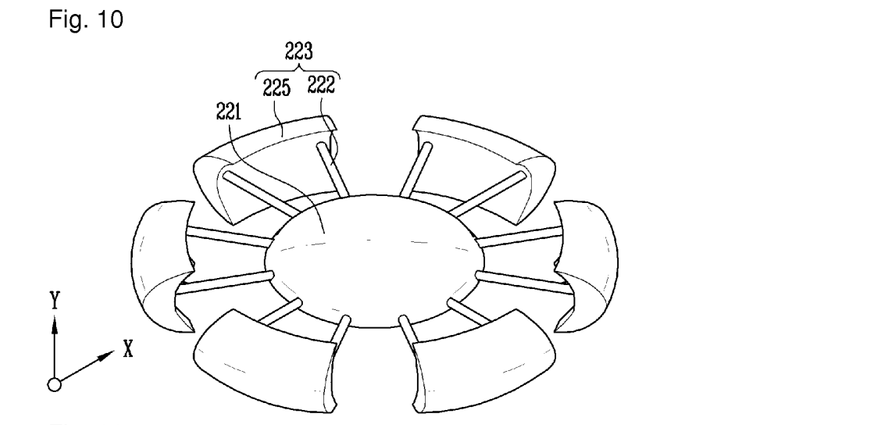
FIG. 10 is a cross-sectional view taken from a line I-I' as shown in FIG. 9.

Referring to FIGS. 9 and 10, the optic portion 221 includes a first optic body 221a having an increasing thickness as its central region approaches its equatorial region, and a second optic body 221b coupled to the first optic body 221a and having at least a thicker thickness in the central region than the first optic body 221a.

At this time, the first optic body 221a includes an inner surface 221ab and an outer surface 221aa, wherein at least the inner surface 221ab preferably is a spherical surface having a larger curvature than the outer surface 221aa, or a more aspheric surface.

To constitute an optic portion 121 composed of two pieces of a first optic body 121a and a second optic body 121b is for the purpose of facilitating a shape deformation of the optic portion 121.

A thickness (L1) of the first optic body 221a is smaller than a thickness (L2) of the second optic body 221b in the section cut along a virtual plane in a visual axis direction (Y direction) of the eye lens. This is for the purpose that the shape deformation of the first optic body 121a is more induced than the second optic body 121b as if the shape deformation of the anterior surface is actually higher in the eye lens if a mechanical or fluent force is transferred to the optic portion 221.

An empty flowing space 231 is provided between the first optic body 221a and the second optic body 221b. The size and shape of the flowing space 231 is associated with the shape of the inner surface of the first optic body 221a and the second optic body 221b. That is to say, If the flowing space 231 is small, at least an anterior surface and a posterior surface of the flowing space 231 is protruded toward the first optic body 221a, and therefore the flowing space 231 starts to be formed into a convex lens shape with an increasing curvature of the anterior surface, and the first face is formed a convex lens shape that is protruded toward the first optic body 221a and the second face is formed a convex lens shape that is protruded toward the second optic body 221b as the flowing space 250 increases in volume.

Since the flowing space is formed in a small scale in FIGS. 9 and 10, the anterior surface and the posterior surface are generally protruded toward a pupil, but the anterior surface is a spherical surface having a larger curvature, or a more aspheric surface, which leads to a convex lens shape as a whole. Meanwhile, the thickness (L2) of the second optic body 221b is desirable to have a larger thickness in its central region if the second optic body 221b is mechanically deformed without any of the flowing space as in the above-mentioned embodiment. However, if the second optic body 221b has a flowing space, namely if the anterior/posterior surfaces has a flowing space ensured in a large scale and formed inside the optic body with an aspheric surface, the second optic body 221b preferably has an increasing thickness as its central region approaches its equatorial region. This is also for the purpose that the optic portion has a structure of a natural eye lens, and the central region of the optic portion makes it easier to shape deformation than the circumferential region, thereby to function more similarly as the natural eye lens.

The haptic portion 223 is coupled to the optic portion 221 from an edge of the optic portion 221, and the haptic portion 223 is composed of a plurality of shaft bars 222 and a support bar 225. The shaft bars 222 of the haptic portion 223 may be provided in at least two numbers to transfer a force to the intraocular lens in balance. At this time, both ends 222a, 222b of the shaft bar 222 preferably has a larger cross-sectional area than the central region. As a result, both ends 222a, 222b of the shaft bar 222 are stably coupled respectively to the optic portion 221 and the support bar 225.

The support bar 225 is a ring-shaped body to which the end 222b arranged opposite to the optic portion 221 of the shaft bar 222 and transferring a force transferred from the capsular sac in more balance, and includes a first face 211 and a second face 213.

Figure 11:
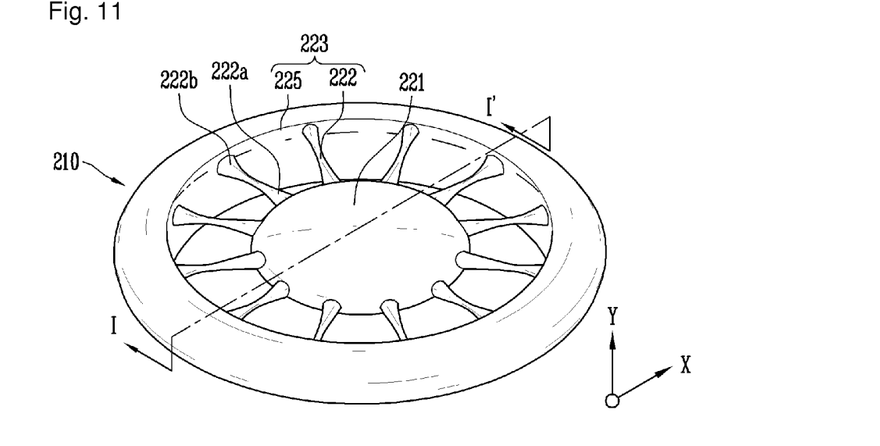
FIG. 11 is perspective view showing an intraocular lens as a modified example of the intraocular lens according to the second embodiment of the present invention.

At this time, the shape of the support bar 225 may be widely varied, and shapes are not limited if the shapes couples at least two ends 222b of the shaft bar 222. That is to say, it is possible to be formed as shown in FIG. 11.

In the intraocular lens according to the first embodiment and the second embodiment, a force transferred from the zonule of Zinn is mechanically transferred to the intraocular lens 210 to control a thickness of the optic portion 221 of the intraocular lens 210.

For the second embodiment, the materials of the intraocular lens may be identical to those of the first embodiment, and their interactions may be easily conducted from the disclosure of the first embodiment by those in the art, and their descriptions are omitted for clarity.

Figure 12:
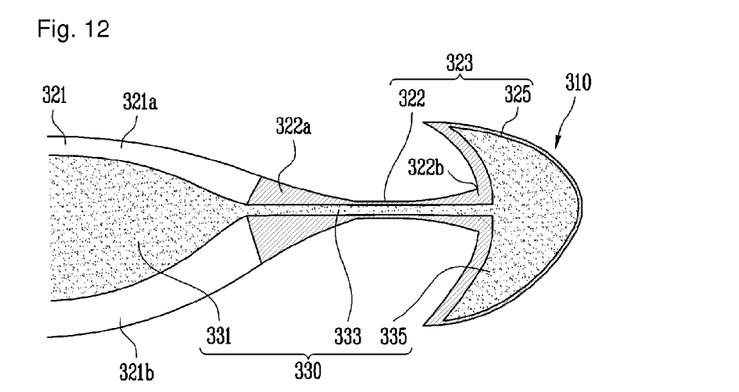
FIG. 12 is a perspective view showing an intraocular lens according to the third embodiment of the present invention.

Meanwhile, in order to make a shape deformation of the intraocular lens in more effective manner, the third embodiment of the present invention will be described in detail. FIG. 12 is a cross-sectional view showing a virtual plane in a visual axis direction of an eye lens of the intraocular lens according to the third embodiment of the present invention.

The intraocular lens 310 according to the third embodiment has a similar structure to the intraocular lens according to the first embodiment or the second embodiment, but the intraocular lens 310 according to the third embodiment is different from the intraocular lens according to the first embodiment or the second embodiment in that a flowing space 350 filled with a fluid is provided inside the intraocular lens 310, and the flowing space 350 may be filled with the fluid.

At this time, the size and shapes of the flowing space 350 may be widely varied. The size and shapes of the flowing space 231 are related to the shape of the inner surfaces of the first optic body 221a and the second optic body 221b. Both of the anterior surface and the posterior surface of the flowing space 231 start to be formed in a convex lens shape that is protruded toward the first optic body 221a as the flowing space 231 gets small, whereas the anterior surface is formed in a convex lens shape that is protruded toward the first optic body 221a and the posterior surface is formed in a convex lens shape that is protruded toward the second optic body 221b as the flowing space increases in volume.

If the flowing space filled with a fluid is provided as described in this embodiment, both of the anterior surface and the posterior surface are preferably formed in a convex lens shape with an aspheric surface.

At this time, thicknesses of the first optic body 221a and the second optic body 221b are increased as their central region approaches their equatorial region.

The fluid filled in the flowing space 350, as used herein, includes water, air, silicone, viscoelastic materials. Examples of the viscoelastic materials, as used herein, may include sodium hyaluronate, chondroitin sulfate, hydroxypropyl methylcellulose, polyacrylamide, etc.

Preferably, the flowing space 330 may be composed of a first space portion 331 formed inside the optic portion 321; second space portion 333 formed inside the connection bar 322; and a third space portion 335 formed inside the support bar 325. The first space portion 331, the second space portion 333 and the third space portion 335 may be coupled, or not coupled to each other, but it is easy to deform the intraocular lens 310 using a fluent force if the first space portion 331, the second space portion 333 and the third space portion 335 are coupled to each other.

In this embodiment, the first space portion 331, the second space portion 333 and the third space portion 335 are coupled to each other. Therefore, the fluid filled in the flowing space 330 allows the first space portion 331, the second space portion 333 and the third space portion 335 of the flowing space 330 to move by external forces.

The fluid filled in the flowing space 350, as used herein, includes water, air, inert gas, silicone, viscoelastic materials. Examples of the inert gas include nitrogen, helium, neon, argon, etc., and examples of the viscoelastic materials, as used herein, may include sodium hyaluronate, chondroitin sulfate, hydroxypropyl methylcellulose, polyacrylamide, etc.

The optic portion 321 may function as a lens with a low power of glasses due to the low refractive index when the first space portion 331 is filled with gas or water, and therefore it is possible to manufacture a negative lens used for the extremely myopic operations.

The second space portion 333 is a space formed in the shaft bar 322. At this time, the shaft bar 322 functions as a kind of a connection tube to allow a fluid to flow between the first space portion 331 and the third space portion 335. The third space portion 335 is a space formed in the support bar 325 as described above, and the third space portion 335 is a region that directly reflects a volume change in the capsular sac. That is to say, the intraocular lens 310 allows a fluid to flow in the flowing space according to the force transferred from the zonule of Zinn since it has the flowing space 330. For example, when focused on a short distance object, the fluid is collected inside the optic portion 321 of the intraocular lens 310, and therefore the optic portion 321 may be deformed more effectively.

Figure 13:
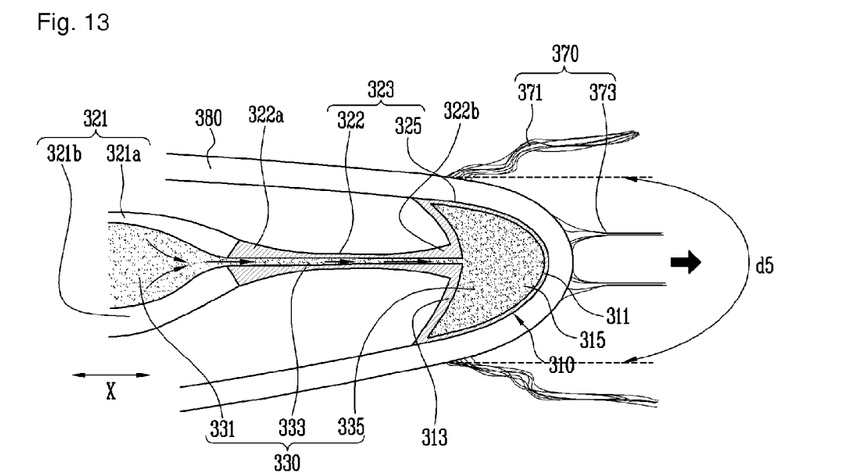
FIG. 13 and FIG. 14 are illustrative views showing interactions of a zonule of Zinn, an intraocular lens and a capsular sac when focused on a respectively long distance and a short distance object according to the third embodiment of the present invention.
Figure 14:
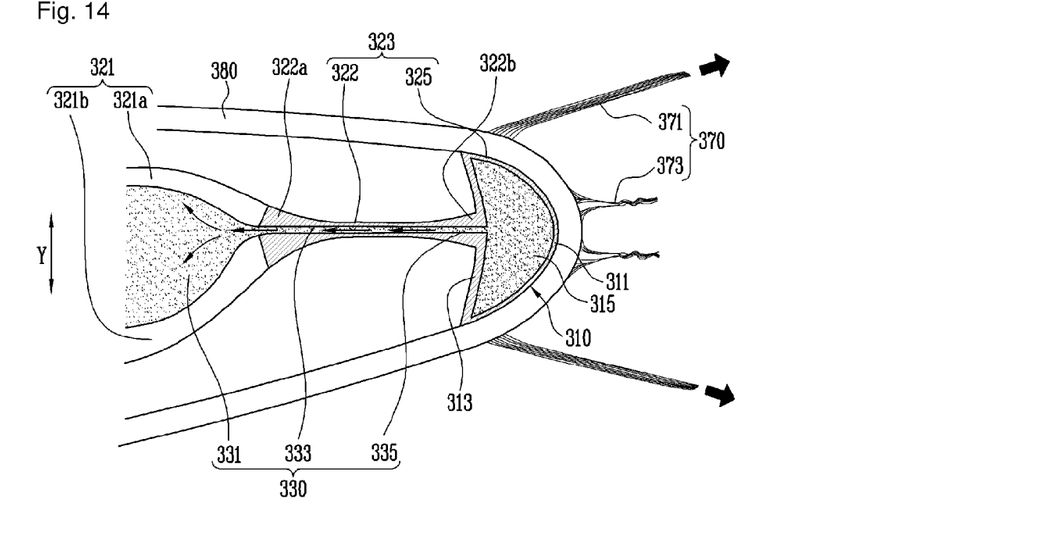

FIG. 13 and FIG. 14 are illustrative views showing interactions of a zonule of Zinn, an intraocular lens and a capsular sac when focused on respectively a long distance and a short distance object according to the third embodiment of the present invention.

When focused on a long distance, a first zonule portion 373 coupled to the center of the equatorial region is pulled taut, and a second zonule portion 171 coupled to a circumference of the equatorial region in the capsular sac 380 is relaxed.

At this time, the equatorial region of the capsular sac 380 is extended in an equatorial direction (X direction) of the eye lens, and a shape of the first face 311 of the support bar in the intraocular lens 310 that is in contact with the capsular sac is also extended in the same direction, which leads to the less convex optic portion 321.

In addition, the fluid filled in the flowing space 330 of the intraocular lens 310 is also subject to external forces, and the intraocular lens 310 is more extended in an equatorial direction of the eye lens when focused on a long distance object, and therefore the fluid in the flowing space 330 is distributed at a higher amount in the third space portion 335 than the first space portion 331 and the second space portion 333. Therefore, the shapes of the optic portions 321; 321a, 321b of the intraocular lens 310 are deformed more effectively to make the optic portion 321 less convex.

When focused on a short distance in the zonule of Zinn, the first zonule portion 373 coupled to the center of the equatorial region of the capsular sac 380 is relaxed, and the second zonule portion 371 coupled to a circumference of the equatorial region of the capsular sac 380 is pulled taut.

Accordingly, the equatorial region of the capsular sac 380 is protruded in a visual axis direction (Y direction) of the eye lens, and therefore the intraocular lens 310 with elasticity arranged inside the capsular sac 380 is also extended in the same direction (Y direction) to be deformed into a suitable shape to see at a short distance.

At the same time, the fluid filled in the flowing space of the intraocular lens 310 is also subject to the external forces. At this time, the fluid in the third space portion 335 is gathered in the first space portion 331 through the second space portion 333 since the external forces are applied to a flexible region of the support bar of the intraocular lens 310 when focused on a short distance, and therefore the shape of the optic portion 321 of the intraocular lens 310 is deformed more effectively to make the optic portion more convex.

Also, if the fluid is gathered in the first space portion 331 of the optic portion 321, the first optic body 321a is formed in a smaller thickness than the second optic body 321b, and therefore the optic portion 321 is made more convex toward the first optic body 321a than the second optic body 321b. As a result, the intraocular lens may be deformed similarly to an actual eye structure. Accordingly, the intraocular lens according to this embodiment may effectively control a shape of the intraocular lens if an ability of the ciliaris muscle is lowered since a force transferred from the zonule of Zinn is mechanically transferred to the intraocular lens 310 and also transferred to the intraocular lens 310 by means of the oil pressure to effectively control a thickness of the optic portion 321 of the intraocular lens 310.

That is to say, an interaction force by a mechanical force complementarily acts together with an interaction force by an oil pressure in this embodiment. The use of more flexible materials, thinner materials or fluids as more flexible media makes the deformation of the optic portion 321 by the oil pressure more increased, and the use of less flexible materials, thicker materials or fluids as more compact media makes the deformation of the optic portion 321 by the mechanical force more increased.

The deformation of the optic portion 321 by the mechanical force is varied with different interaction forces according to the shapes and positions of the above-mentioned materials inserted into the optic portion 321 by the end 322a in the optic portion of the shaft bar 322. At this time, the shape deformation of the optic portion 321 is made in a large scale but its stability is low if the interaction force is high, whereas the shape deformation of the optic portion 321 is made in a small scale but its stability is high if the interaction force is low.

The suitable materials and fluids may be selected to adjust a control ability of the intraocular lens since the deformation of the optic portion 321 is made in a higher level by the oil pressured other than the mechanical force.

The intraocular lens with very high control ability has a disadvantage that it has a short lift span due to the repeated excessive deformation and the thin materials of the optic portion, but it is suitable for old patients who has a poor control ability of the eye. Accordingly, the intraocular lens according to this embodiment may control a thickness of the optic portion 321 of the intraocular lens since a force transferred from the zonule of Zinn is transferred to the intraocular lens mechanically or fluently.

Even in the third embodiment, materials of the intraocular lens may be applied in the same manner as described above.

Figure 15:
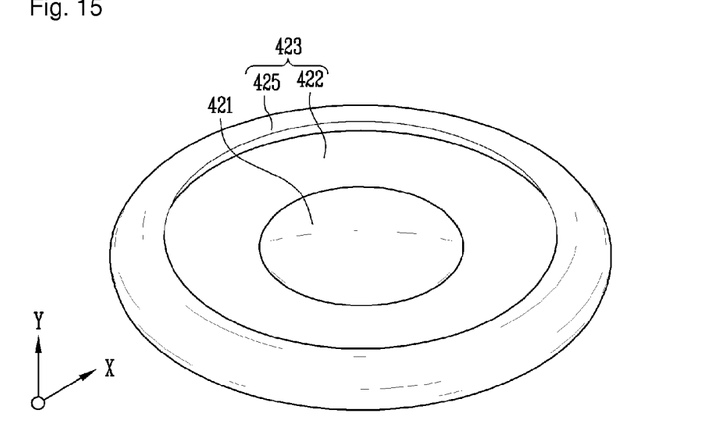
FIG. 15 is a perspective view showing an intraocular lens according to the fourth embodiment of the present invention.

FIG. 15 is a perspective view showing an intraocular lens according to the fourth embodiment of the present invention. Unlike the above-mentioned embodiments, the connection bar 422 is configured with a disk-shaped structural body in the fourth embodiment. In this case, the support bar 425 formed in an end of the connection bar 422 may be a ring-shaped structural body formed in the entire circumference of the disk-shaped structural body, or formed in some section of the circumference.

Figure 16:
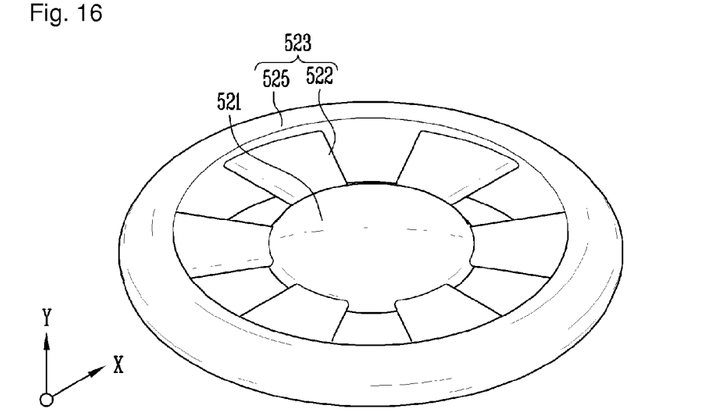
FIG. 16 is a perspective view showing an intraocular lens according to the fifth embodiment of the present invention.

FIG. 16 is a perspective view showing an intraocular lens according to the fifth embodiment of the present invention. Unlike the above-mentioned embodiments, the connection bar 522 is composed of divided disk-shaped structural bodies that are coupled to one section of the optic portion 521 in the fifth embodiment. Even in this case, the support bar 525 formed in an end of the connection bar 522 may be a ring-shaped structural body formed in the entire circumference of the disk-shaped structural body, or formed in some section of the circumference.

Figure 17:
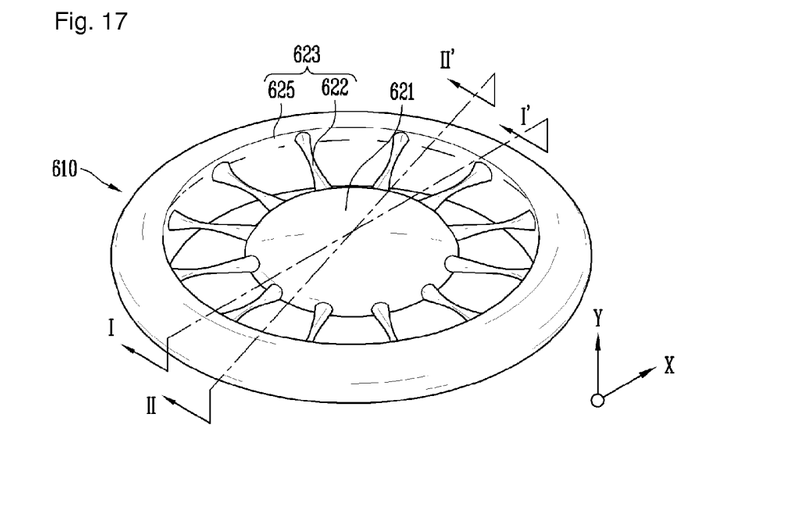
FIG. 17, FIG. 18 and FIG. 19 are is a perspective view showing an intraocular lens according to the sixth embodiment of the present invention, and cross-sectional views showing virtual planes in a visual axis direction of the eye lens.
Figure 18:
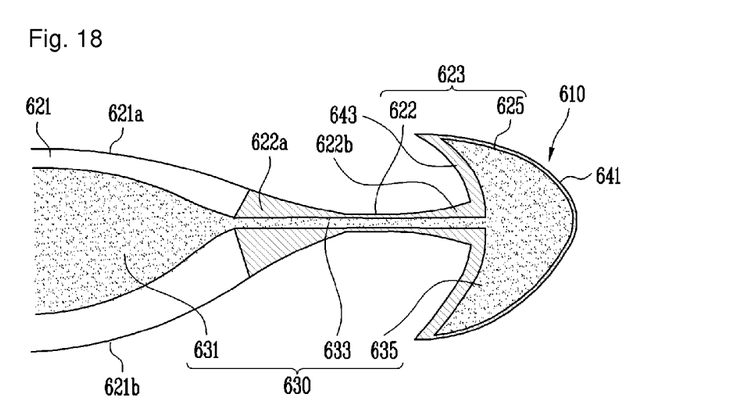
Figure 19:
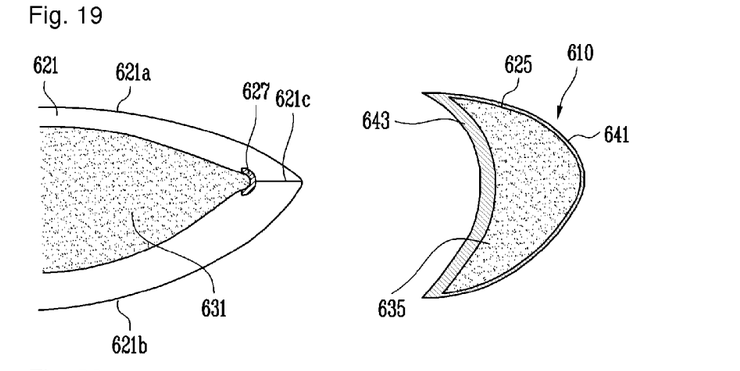
Figure 20:
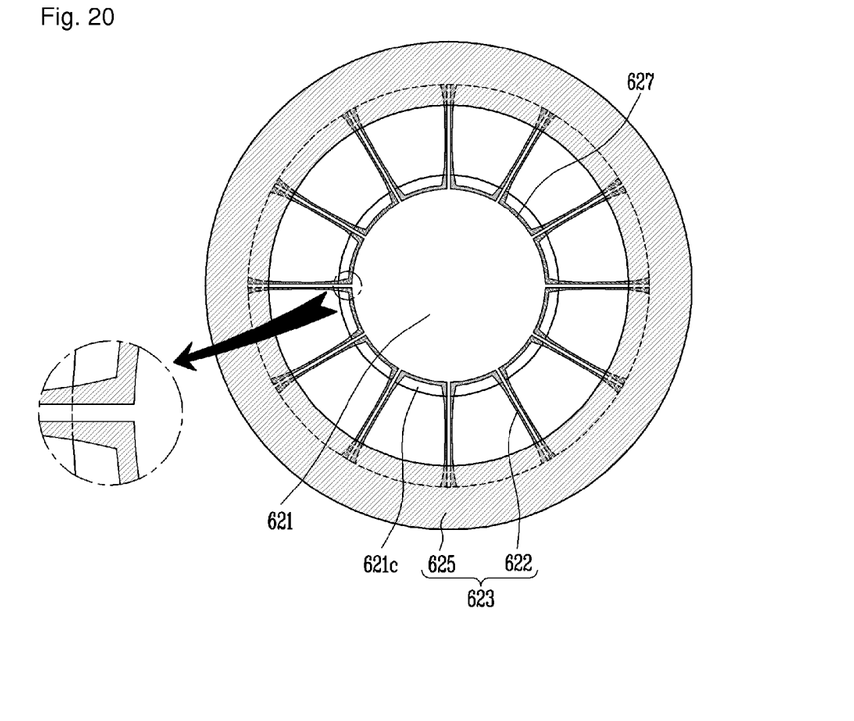
FIG. 20 is a cross-sectional view showing virtual planes in an equatorial direction of the eye lens of the intraocular lens according to the embodiment as shown in FIG. 17.

FIG. 17 is a perspective view showing an intraocular lens according to the sixth embodiment of the present invention, and FIGS. 18 and 19 are cross-sectional views taken from lines I-I' and II-II' as shown in FIG. 17, respectively. Also, FIG. 20 is a cross-sectional view where the intraocular lens as show in FIG. 17 is cut along a virtual plane in an equatorial direction of the eye lens. Referring to FIGS. 17 and 20, this embodiment is different from the above-mentioned embodiments in that the intraocular lens according to this embodiment has a second support bar 627.

The optic portion 621 includes a first optic body 621a and a second optic body 621b, and the haptic portion 623 is then configured to include a first support bar 625, a second support bar 627 and a shaft bar 622.

The optic portion 621 includes a first optic body 621a and a second optic body 621b, which have an increasing thickness as its central region approaches its equatorial region.

At this time, the posterior surface of the first optic body 621a and the anterior surface of the second optic body 621b are preferably aspheric surfaces.

Also, the first optic body 621a and the second optic body 621b may have different convexity. That is to say, the first optic body 621a and the second optic body 621b may be different from each other like an anterior surface and a posterior surface of a human eye lens, but a curvature of the anterior surface is preferably smaller than the posterior surface.

Meanwhile, shapes of the optic portion 621 are not limited thereto, but the optic portion 621 is preferably provided in a conventional convex lens shape. In this case, a diameter of the optic portion 621 may be provided in a diameter as much as 0.2 to 0.8 times of the total diameter of the intraocular lens 610.

To constitute an optic portion 621 composed of two pieces of a first optic body 621a and a second optic body 621b is for the purpose of facilitating a shape deformation of the optic portion 621. At this time, a first space portion 631 through which a fluid may flow is included between the first optic body 621a and the second optic body 621b of the optic portion 621.

The haptic portion 623 is coupled to the optic portion 621 so that some portion of the optic portion 621 is included inside the haptic portion 623, and the haptic portion 623 is composed of a plurality of shaft bars 622, a first support bar 625 and a second support bar 627. The shaft bars 622 of the haptic portion 623 is provided in at least two numbers to transfer a force to the intraocular lens in balance, and includes a second space portion 633 as a flowing space formed inside of it.

The first support bar 625 is provided to transfer a force transferred from the capsular sac in more balance, as described above in the above embodiments. The first support bar 625 has a first face 641 coming in contact with the inner surface of the capsular sac in at least one point; and a second face 643 arranged opposite to the first face 641, and, as the ring-shaped structure to which an end 622b arranged opposite to the optic portion of the shaft bar 622, its outer surface is preferably in a circular shape, and its inside may include a third space portion 635.

As described above, in a section where the structural body is cut along a virtual plane in a visual axis direction (Y direction) of the eye lens, the first support bar 625 is preferably provided at a length as much as at least ¾ to 3 times of a length of a section in a region where a zonule of Zinn is coupled to an outer surface of the capsular sac.

The second support bar 627 couples ends 622a in the optic portion of the shaft bar 622 to the haptic portion of the intraocular lens 610 to give stability to the shaft bar 622, thereby to transfer a force, transferred through the shaft bar 622, to the optic portion 621 in more balance. At this time, the second support bar 627 may be a structural body that couples the ends 622a in the optic portion of the shaft bar 622, or couples shaft bars 622 around the ends to each other. Also, a surface where the second support bar 627 is in contact with the optic portion preferably has a shape corresponding to an equatorial surface of the optic portion, namely a shape that is concave toward the center of the optic portion.

If the optic portion 621 and the haptic portion 623 are made of different materials, the end 622a in the optic portion of the shaft bar 622 maximizes its mechanical control ability, and some of the end 622a may be included inside the optic portion 621 for the purpose of the stability of the optic portion 621 in manufacturing the shaft bar 622. At this time, in manufacturing the optic portion 621, the first optic body 621a and the second optic body 621b are met and pressured to form an optic junction 621c in a circumferential region regardless of the flowing space.

Accordingly, the optic junction 621c functions to reduce a mechanical or oil pressure deformation in the optic portion 621, but to cause a mechanical or oil pressure deformation more effectively and intensively in the central region where the first optic body 621a and the second optic body 621b are attached to each other.

Also, shapes coupled to the optic portion of the shaft bar 622 may be widely varied, and the control ability by the mechanical force may be different according to the shapes.

That is to say, the deformation of the optic portion 621 by the mechanical force is varied with different interaction forces according to the shapes and positions of the above-mentioned materials surrounding the circumference of the optic portion 621 by means of the end 622a in the optic portion of the shaft bar 622. At this time, the shape deformation of the optic portion 621 is made in a large scale but its stability is high if the interaction force is high, whereas the shape deformation of the optic portion 621 is made in a small scale but its stability is very high if the interaction force is low.

The end 622a in the optic portion of the shaft bar 622 may be in various shapes such as a convex cone, a convex sphere, circular cylinder, a concave sphere and a concave cone, and the above-mentioned control ability by the mechanical force is varied according to the shapes. In the case of this embodiment, the end 622a in the optic portion has a conical shape toward the optic portion 621, as shown in FIG. 18, and has a cylindrical shape in an exploded diagram of FIG. 20. Meanwhile, the shaft bar 622 of the haptic portion 623 is made of relatively more rigid materials than the optic portion 621, or the first support bar 625 and the second support bar 627, or has suitable elasticity and restoring force for the mechanical deformation. Also, materials constituting the first face 641 of the first support bar 625 and the optic portion 621 are preferably more flexible than materials constituting the second face 643 of the first support bar 625 and the second support bar 627.

As a result, this is for the purpose of effectively deforming the shape of the optic portion 621 using the force transferred by the movement of the zonule of Zinn induced in the ciliaris muscle. Here, the term flexible means that a material is so soft to deform easily. In addition, the second face 643 is provided in a larger thickness than the first face 641. This is for the purpose of functioning as a wheel capable of making the second face 643 less flexible and strongly fixing the shaft bar 622 in the first support bar 625 at the same time.

Also, the movement of the zonule of Zinn may be reflected more sensitively since a flowing space is provided inside the optic portion 621 and the haptic portion 623, as described above.

The intraocular lenses according to the above-mentioned embodiments of the present invention may be formed into one piece as described above, or formed with several pieces. For example, if the intraocular lens is formed into one piece, it may be manufactured using various plastic forming methods, and if the intraocular lens is formed with several pieces, it may also be easily manufactured through the attachment of the pieces using an adhesive, a heat, a laser, etc.

The description proposed herein is just a preferable example for the purpose of illustrations only, not intended to limit the scope of the invention, so it should be understood that other equivalents and modifications could be made thereto without departing from the spirit and scope of the invention as apparent to those skilled in the art. Therefore, it should be understood that the present invention might be not defined within the scope of which is described in detailed description but within the scope of which is defined in the claims and their equivalents.

The invention claimed is:

1. An intraocular lens adapted to be inserted inwardly into a capsular sac, comprising:
    an optic portion including a first optic body whose central region has a smaller thickness than a circumference of the central region and a second optic body coupled to the first optic body and whose central region has the same or higher thickness as/than the central region of the first optic body; and
    a haptic portion including a connection bar coupled to the optic portion and first support bar coupled to a circumference of the connection bar to be in contact with an inner surface of the capsular sac when inserted into the capsular sac, and a first face arranged opposite to a second face, and
    the first face provided at a length ¾ to 3 times a length of a region where a zonule of Zinn would be coupled to an outer surface of the capsular sac in a section where the first support bar is cut along a virtual plane in a visual axis direction (Y) of an eye lens when inserted into the capsular sac,
    the first face having an anterior portion and a posterior portion which corresponds respectively to an anterior capsule and a posterior capsule of the capsular sac when inserted into the capsular sac, divided by an equator (E) of the capsular sac, wherein the equator (E) is a vertical direction (X) relative to the visual axis direction (Y) of the eye lens,
    wherein the anterior portion has a larger curvature than the posterior portion in the section where the first face is cut along the virtual plane in the visual axis direction (Y) of the eye lens,
    the first face has a first extended length from one end portion to the other end portion in the section where the first face is cut along the virtual plane in the visual axis direction (Y) of the eye lens of 2 to 8.4 mm, and
    the second face has a second extended length from one end portion to the other end portion in the section where the second face is cut along the virtual plane in the visual axis direction (Y) of the eye lens, and
    the second extended length of the second face is smaller than or identical to the first extended length of the first face and the second extended length of the second face is longer by 0.4 to 1 times the first extended length of the first face.

2. The intraocular lens according to claim 1, wherein the first optic body is made of materials that are more flexible than the second optic body.

3. The intraocular lens according to claim 1, wherein the first optic body includes an inner surface and an outer surface, the inner surface and the outer surface are a spherical surface or an aspheric surface, and the inner surface is a spherical surface having a higher curvature than the outer surface, or a more aspheric surface than the outer surface.

4. The intraocular lens according to claim 1, wherein the first support bar has a surface that is adapted to be in contact with an inner surface of the capsular sac and has a round shape.

5. The intraocular lens according to claim 1, wherein the connection bar is a shaft bar-shaped structural body coupled to at least two sections in a circumference of the optic portion.

6. The intraocular lens according to claim 5, wherein the first support bar is a structural body for coupling at least two ends of the shaft bars arranged opposite to the optic portion of the connection bar.

7. The intraocular lens according to claim 5, wherein the first support bar is a ring-shaped structural body for coupling all ends of the shaft bars arranged opposite to the optic portion of the connection bar.

8. The intraocular lens according to claim 5, wherein ends of the optic portion of the shaft bar include a second support bar for coupling ends of the optic portion.

9. The intraocular lens according to claim 8, wherein an inner surface of the second support bar has a concave shape toward the central region of the optic portion.

10. The intraocular lens according to claim 8, wherein the second support bar is coupled to a circumference of the optic portion.

11. The intraocular lens according to claim 8, wherein the second support bar is inserted inwardly into the optic portion.

12. The intraocular lens according to claim 5, wherein both ends of the shaft bar have a larger cross-sectional area than a central region of the shaft bar.

13. The intraocular lens according to claim 1, wherein the connection bar is a disk-shaped structural body coupled to the entire section of the circumference of the optic portion.

14. The intraocular lens according to claim 1, wherein the connection bar is a disk-shaped structural body coupled to at least two sections of the circumference of the optic portion and divided into at least two sections.

15. The intraocular lens according to claims 13 or 14, wherein the first support bar is formed around an end of the disk-shaped connection bar.

16. The intraocular lens according to claim 1, wherein the optic portion and the first support bar are made of flexible materials that is more flexible than a material of the connection bar.

17. The intraocular lens according to claim 1, wherein the optic portion and the first support bar are made of the same flexible materials as the connection bar, and formed in a thinner thickness than the connection bar.

18. The intraocular lens according to claim 1, wherein the first face is made of flexible materials that more flexible than the second face.

19. The intraocular lens according to claim 18, wherein a sectional shape of the first face of the first support bar accords with an inner surface of the capsular sac when the sectional shape of the first face is in contact with the inner surface of the capsular sac in the section where the intraocular lens is cut along a virtual plane in a visual axis direction (Y direction) of the eye lens.

20. The intraocular lens according to claim 1, wherein the first face is made of the same flexible materials as the second face, and formed in a thinner thickness than the second face.

21. The intraocular lens according to claim 1, wherein the first face is made of the same flexible materials as the second face, and formed in the same thickness as the second face.

22. The intraocular lens according to claim 1, wherein a surface of the first face is rougher than the other surface.

23. The intraocular lens according to claim 1, wherein the surface of the first face further includes an adhesive for facilitating mounting of the capsular sac.

24. The intraocular lens according to claim 23, wherein the adhesive is tissue glue or glue.

25. The intraocular lens according to claim 1, wherein a flowing space is provided inside the intraocular lens.

26. The intraocular lens according to claim 25, wherein the flowing space is provided at least between the first optic body and the second optic body.

27. The intraocular lens according to claim 26, wherein the second optic body has a thinner thickness in its central region than its circumference.

28. The intraocular lens according to claim 27, wherein the second optic body includes a section that grows thicker as its equatorial region approaches its circumference.

29. The intraocular lens according to claim 26, wherein the second optic body includes an inner surface and an outer surface, and the inner surface and the outer surface are a spherical surface or an aspheric surface, and the inner surface is a spherical surface or an aspheric surface that has a larger curvature than the outer surface.

30. The intraocular lens according to claim 26, wherein the first optic body and the second optic body have the same thickness, and include sections that have an increasing thickness as their central regions approach their circumference, respectively.

31. The intraocular lens according to claim 25, wherein the flowing space includes a first space portion provided between the first optic body and the second optic body; a second space portion provided inside the connection bar; and a third space portion provided inside the first support bar.

32. The intraocular lens according to claim 31, wherein the first space portion, the second space portion and the third space portion are coupled to each other.

33. The intraocular lens according to claim 31, wherein the flowing space is filled with one selected from the group consisting of liquid, gas, and fluent solid.

34. The intraocular lens according to claim 33, wherein the liquid is one selected from the group consisting of water, silicone, sodium hyaluronate, chondroitin sulfate, hydroxypropyl methylcellulose and polyacrylamide.

35. The intraocular lens according to claim 33, wherein the gas is one selected from the group consisting of air, nitrogen, helium, neon and argon.

36. The intraocular lens according to claim 31, wherein the first space portion has at least one convex surface.

37. The intraocular lens according to claim 36, wherein the first space portion has at least one aspheric surface.

38. The intraocular lens according to claim 1, wherein at least one face out of the first face and the second face is protruded in a direction from the second face toward the first face.

39. The intraocular lens according to claim 1, wherein a material of the intraocular lens is composed of one selected from the group consisting of silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethyleneglycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

40. The intraocular lens according to claim 1, wherein the first optic body includes a section that grows thicker as its equatorial region approaches its circumference.

* * * * *